United States Patent [19]

Quinlan

[11] 4,342,584
[45] Aug. 3, 1982

[54] MICROBIOCIDAL PROCESS USING DI-QUATERNARY AMMONIUM SALTS OF α-1,4-THIAZINE ALKANEPHOSPHONIC ACIDS

[75] Inventor: Patrick M. Quinlan, Webster Groves, Mo.

[73] Assignee: Petrolite Corporation, St. Louis, Mo.

[21] Appl. No.: 196,973

[22] Filed: Oct. 14, 1980

Related U.S. Application Data

[62] Division of Ser. No. 932,259, Aug. 9, 1978, Pat. No. 4,264,768.

[51] Int. Cl.$^3$ .................. A01N 57/00; A01N 57/26
[52] U.S. Cl. ................................. 71/67; 71/86; 424/200

[58] Field of Search .............. 71/67, 86; 424/200; 542/412

[56] References Cited

U.S. PATENT DOCUMENTS

| 3,539,561 | 1/1970 | Budde et al. | 544/57 |
| 3,652,742 | 3/1972 | Sirrenberg et al. | 544/57 |
| 3,658,800 | 4/1972 | Beriger | 544/57 |

*Primary Examiner*—Leonard Schenkman
*Attorney, Agent, or Firm*—Sidney B. Ring; Hyman F. Glass

[57] ABSTRACT

This invention relates to novel di-quaternary ammonium salts of α-1,4-thiazine alkanephosphonic acids; the preparation thereof; and uses thereof.

6 Claims, No Drawings

MICROBIOCIDAL PROCESS USING DI-QUATERNARY AMMONIUM SALTS OF α-1,4-THIAZINE ALKANEPHOSPHONIC ACIDS

This is a division, of application Ser. No. 932,259, filed Aug. 9, 1978, now U.S. Pat. No. 4,264,768.

This invention relates to novel di-quaternary ammonium salts of α-1,4-thiazine alkanephosphonic acids of the formula:

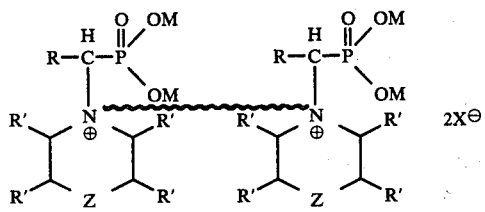

where R is a hydrocarbon or a substituted hydrocarbon group for example alkyl, alkenyl, cycloalkyl, aryl, aralkyl, substituted aryl, etc., the R's are hydrogen or a substituted group such as a hydrocarbon group, i.e., alkyl, etc.; ∼∼∼ is a bridging group for example a hydrocarbon group such as alkylene, alkenylene, alkaralkylene or hydrocarbon groups also containing other elements than carbon and hydrogen, Z is S,

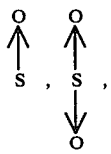

M is hydrogen, or a salt moiety such as alkali metal, alkaline earth metal, alkyl-ammonium, or ammonium and X is an anion such as halide, acetate, sulfonate, aralysulfonate, etc.; and to the preparation and uses thereof.

These compounds are prepared by reacting 2 mols of an α-1,4-thiazine alkanephosphonic acid compound with one mol of di-alkylating agent in a suitable polar solvent or a mixture of polar solvents. The preparation of α-1,4-thiazine alkanephosphonic acids is described in Ser. No. 932,257 filed Aug. 9, 1978. The reaction may be illustrated by the following equation:

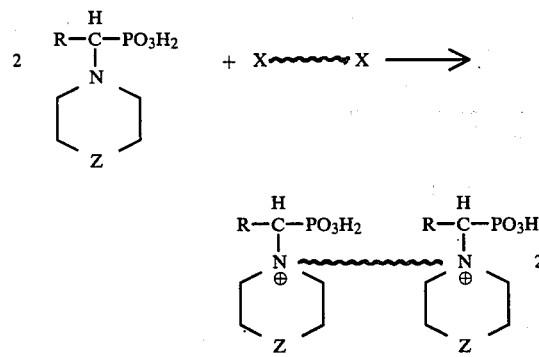

Examples of the divinyl sulfur compounds include

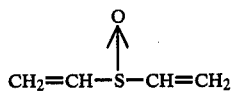

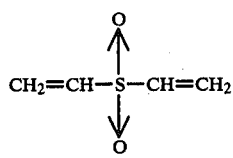

Solvents useful in the method of this invention are water, mixtures of water and lower alcohols, lower alcohols, dimethyl formamide, dimethyl sulfoxide, etc.

After combining the reactants in a suitable reactive medium, the reaction mixture is heated to from 50° C. to 150° C. with stirring to promote the alkylation reaction.

After the reaction is complete, the di-quaternary ammonium product may be isolated or used as is in the practice of this invention.

The quaternary nitrogen are joined together by any suitable bridging means, such as for example a hydrocarbon group such as alkylene, alkenylene, aryl group such as alkaryalkylene such as

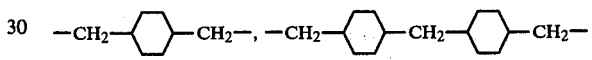

etc., or hydrocarbon group containing other than carbon and hydrogen, for example alkyletheralkylene such as

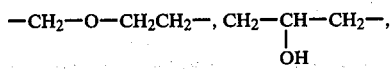

X∼∼∼X may be a wide variety of polymerizing compounds, i.e., capable of joining amino groups, where ∼∼∼ may be alkylene, alkenylene, alkynylene, alkaralkylene, an alkyleneether-containing group, an ester-containing group, etc., and X is a halide.

The following are non-limiting examples:

(I) Saturated dihalides

where ∼∼∼ is alkylene, straight chain or branched, for example $X(CH_2)_nX$ where n is 2–25 or more, for example 2–10, but preferably 2–4. The

may be branched such as where at least one of the H's is a hydrocarbon group such as alkyl, i.e., methyl, ethyl, etc., substituted such as halo, hydroxy, etc.

(II) Aralkylene dihalides

where Z is aralkylene having for example 8–30 or more carbons, such as 8–20 carbons, but preferably xylylene.

The following are illustrative examples:

$-CH_2-\langle cyclohexane \rangle-CH_2-$ $-CH_2-\langle decalin \rangle-CH_2-$ $\langle cyclohexane \rangle(-CH_2-)(-CH_2-)$ $-CH_2-\langle cyclohexane \rangle(-CH_2-)(-CH_2-)(-CH_2-)$ $-CH_2-\langle cyclohexane-OH \rangle-CH_2-$ $-CH_2-\langle cyclohexyl-cyclohexyl \rangle-CH_2-$ Additional examples of aralkylene radicals include those of the formula —CH₂—Ar—CH₂— where Ar is $\langle C_6H_{6-X}, X_{1-4}\rangle$ (X = halogen), $\langle C_6H_{6}, alkyl_{1-4}\rangle$, $\langle C_6H_{6}, alkyl_m, X_n\rangle$, $\langle C_6H_{6}, OH, alkyl_{1-4}\rangle$ (where n + m = 1-4)

$\langle naphthalene, X_{1-4}\rangle$, $\langle tetralin, alkyl_{1-4}\rangle$, $\langle decalin, X_{1-2}, alkyl_{1-3}\rangle$ $\langle C_6H_5\rangle-CH_2-\langle C_6H_5\rangle$ $\langle C_6H_5\rangle-O-\langle C_6H_5\rangle$ $\langle C_6H_5\rangle-SO_2-\langle C_6H_5\rangle$ (III) Alkylene ethers

X—A—X where A is an alkyleneether radical —A(OA)ₙ where A is alkylene (including cycloalkylene ether radicals) having for example from 1-10 or more carbons such as 1-4, but preferably 2 in each alkylene unit. Typical examples are Cl—CH₂CH₂—O—CH₂CH₂—Cl
Cl—CH₂CH₂(OCH₂CH₂)₁₋₁₀—Cl $$Cl-CH\underset{O}{\overset{CH_2-CH_2}{<\quad>}}CH-Cl$$

Cl—CH₂CH₂O—CH₂O—CH₂CH₂—Cl

Additional examples of A include groups of the formula (AO)ₙ where A is $$-\overset{Y}{\underset{|}{CH}}-CH_2-$$

where Y is alkyl, for example $$-\overset{CH_3}{\underset{|}{CH}}-CH_2-,\quad \overset{CH_3}{\underset{|}{CH_2}}\atop{-CH-CH_2-},\quad \overset{CH_3}{\underset{|}{(CH_2)_5}}\atop{-CH-CH_2}$$

etc.

Thus, A can be methylene, polymethylene, ethylene, propylene, butylene, octylene, etc. In addition (AO)ₙ may be homo or hetero as to A, to yield for example (ETO)$_a$(PrO)$_b$, (PrO)$_a$(BuO)$_b$, or (PrO—ETO)$_n$;

—CH₂OCH₂CH₂OCH₂CH₂OCH₂— etc.

These compounds also include the formal of ethylene chlorohydrin and bromohydrin, for example ClCH₂CH₂OCH₂OCH₂CH₂Cl,
ClCH₂CH₂OCH₂CH₂OCH₂OCH₂CH₂OCH₂CH₂Cl etc.

(IV) Unsaturated dihalides

X~~~~X where ~~~~ is an unsaturated aliphatic radical, for example

—CH₂—CH=CH—CH₂—

—CH₂—C≡C—CH₂— etc.

The reaction is illustrated by the following examples.

EXAMPLE 1

Into a flask equipped with a mechanical stirrer, heating jacket, and reflux condenser are charged 48.6 g. (0.2 mol) of

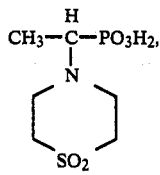

21.6 g (0.1 mol) of 1,4-dibromobutane, 35 g. of water and 35 g. of 2-propanol. The reaction mixture was heated to reflux and held there for 8 hours. The reaction mixture was stripped of volatiles in vacuo. The resulting solid was washed several times in methanol. It was recrystallized several times from aqueous ethanol. The structure of the product was indicated to be:

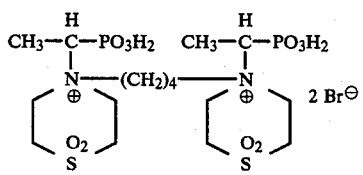

Anal. Calculated; N, 4.00; P, 8.83; Br, 22.79 Found; N, 3.85; P, 8.65; Br, 22.54.

EXAMPLE 2

Into a suitable reaction vessel were charged 51.4 g. (0.2 mol) of

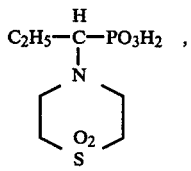

24.4 g. (0.1 mol) of 1,6-dibromohexane, 50 ml. of water and 50 ml. of ethanol. The reaction mixture was heated to reflux and held there for 8 hrs. The product was:

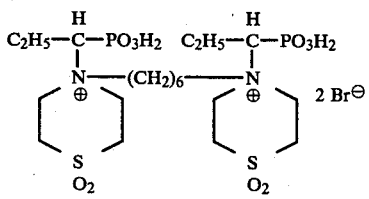

EXAMPLE 3

Into a suitable reaction vessel were charged 51.4 g. (0.2 mol) of

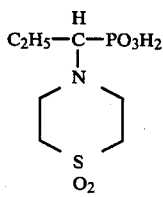

12.5 g. (0.1 mol) of 1,4-dichlorobutane-2, 50 ml. of 2-propanol and 25 ml. of water. The reaction mixture was heated to reflux and held there for 8 hrs. The product was:

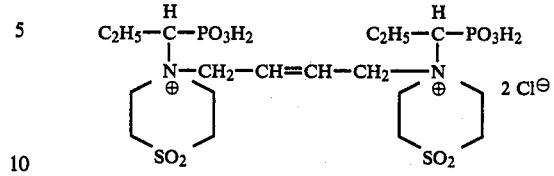

Since the examples described herein are similarly prepared, they will be presented in the following table.

| | | | |
|---|---|---|---|
| Example | R | ～～～ | X |
| 4 | $CH_3$ | $(CH_2)_6$ | Br |
| 5 | $CH_3$ | $H_2C-\phi-CH_2$ | Cl |
| 6 | phenyl | $(CH_2)_4$ | Br |
| 7 | $CH_3$ | $(CH_2)_4$ | Br |
| 8 | $C_3H_7$ | $(CH_2)_4$ | Br |
| 9 | $C_3H_7$ | $CH_2CH=CHCH_2$ | Cl |
| 10 | $C_{11}H_{23}$ | $(CH_2)_4$ | Br |
| 11 | $C_{11}H_{23}$ | $CH_2CH=CHCH_2$ | Cl |
| 12 | $C_{17}H_{33}$ | $(CH_2)_4$ | Br |

USE AS A SCALE INHIBITOR

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 2.5 p.p.m.

The compounds of the present invention (i.e., the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or with alkaline earth metal ions which may be converted into the corresponding sodium salt by the addition of sodium hydroxide. If the pH of the amine compound is adjusted to 7.0 by the addition of caustic soda, about one half of the —OH radicals on the phosphorous atoms will be converted into the sodium salt form.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 p.p.m. to about 50,000 p.p.m. of scale-forming salts. The compounds of the present invention effectively inhibit scale formation when present in an amount of from 0.1 to about 100 p.p.m., and preferably 0.2 to 50 p.p.m. wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 p.p.m. There is no reason to believe that this is the minimum effective concentration. The scale inhibitors of the present invention are effective in both brine, such as sea water, and acid solutions.

The following examples are presented to illustrate the use of the phosphonates prescribed herein and are presented for purposes of illustration and not of limitation.

The following test was used to evaluate these compositions as scale inhibitors. Procedure:

1. Make up stock $CaCl_2.2H_2O$, 2.94 g/L or 56 g/5 gallons (18.9 liters)
2. Stock $NaHCO_3$ should be 3.35 g/L or 64 g/5 gallons.
3. Inhibitors—Make 0.1 percent solutions in deionized water. 1 ml in 100 sample = 10 p.p.m. (Test at 5, 20, and 50 p.p.m.).

Put 50 ml bicarbonate solution into 100 ml milk dilution bottle. Add inhibitor (for 100 ml final volume). Then add 50 ml $CaCl_2$ solution and set in bath at 180° F. Do not cap. Always prepare a blank. Run a hardness determination on a 50—50 mixture before heating.

Heat at 180° F. Take 10 ml samples from bottles after 2 hours and 4 hours.

Filter through millipore filter.
Run total hardness on filtrate.
Calculate as % Ca still in solution, i.e., $$\frac{\text{Total hardness after heating}}{\text{Total hardness before heating}} \times 100 = \%$$

The Compounds were tested at 180° F. at the concentrations indicated. Hardess readings were taken after 2 and 4 hours.

TABLE A

| Compound | Scale Inhibitor Tests | |
|---|---|---|
| | Concentration | % Protection |
| Example 1 | 5 p.p.m. | 30 |
| | 50 p.p.m. | 60 |
| Example 1 (sodium salt) | 50 p.p.m. | 55 |
| Example 2 | 5 p.p.m. | 29 |
| | 50 p.p.m. | 58 |
| Example 3 (sodium salt) | 5 p.p.m. | 31 |
| Example 8 (sodium salt) | 5 p.p.m. | 30 |
| | 50 p.p.m. | 57 |
| Typical Commercial Inhibitor | 5 p.p.m. | 24 |
| | 50 p.p.m. | 30 |

USE IN THE CHELATION OR SEQUESTRATION OF METAL IONS

The chelating or sequestering agents of the present invention are of wide utility such as when it becomes necessary to sequester or inhibit the precipitation of metal cations from aqueous solutions. Among their many uses are the following applications:

Soaps and detergents, textile processing, metal cleaning and scale removal, metal finishing and plating, rubber and plastics industry, pulp and paper industry, oil well treatment, chelation in biological systems.

An important function of these compounds is their ability to sequester $Fe^{+2}$. In secondary oil recovery by means of water floods, waters are frequently mixed on the surface prior to injection. Frequently these waters contain amounts of $Fe^{+2}$ and $H_2S$. If these incompatible waters are mixed, an FeS precipitate results which can plug the sand face of the injection well. Another of their functions is to provent formation of gelatinous iron hydroxides in the well and in the effluent production waters.

To demonstrate the effectiveness of the di-quaternary ammonium salts of the present invention in chelating $Fe^{+2}$, the following test procedure was utilized. Into a flask that contained a known concentration of the sequestering agent, and enough sodium hydroxide or hydrochloric acid to give the desired pH was placed a 100 ml. aqueous sample of ferrous ammonium sulfate (20 p.p.m. of $Fe^{+2}$); after final pH adjustment the solution was allowed to remain at ambient temperatures for 48 hours. The solution was centrifuged for one hour to remove collodial iron hydroxide and an aliquot of the supernatant solution was analyzed by atomic absorption to determine the iron concentration.

The following table illustrates the ability of the sequestering agents of the present invention to sequester $Fe^{+2}$, as compared to the well known sequestering agent tetra-sodium ethylenediamine tetra-acetate (EDTA).

TABLE I

| pH | Sequestering agent (p.p.m.) | Amount of iron sequestered (p.p.m.) |
|---|---|---|
| 5 | Ex. 1 (50) | 10 |
| | Ex. 2 (50) | 10 |
| | EDTA (50) | 7 |
| 7 | Ex. 1 (50) | 10 |
| | Ex. 3 (50) | 9 |
| | EDTA (50) | 7 |
| 10 | Ex. 1 (150) | 8 |
| | Ex. 3 (150) | 7 |
| | EDTA (150) | 6 |

As one can observe from the preceding table, the sequestering agents of this invention are as effective, and in some cases superior, to EDTA when tested over a wide pH range.

The sequestering agents of this invention are also quite effective in sequestering other metal cations in aqueous solutions. For example, a test was conducted in which 60 p.p.m. of the sequesterant were dissolved in 100 ml. of water. The pH was adjusted to 9 and maintained there. Metal cations were added, in the following amounts, before a noticeable precipitate was formed.

TABLE II

| Sequesterant, product of | Metal (p.p.m.) sequestered per 60 p.p.m. sequesterant |
|---|---|
| Example 1 | $Fe^{+3}$ (60) |
| | $Al^{+3}$ (100) |
| | $Cu^{+2}$ (100) |
| | $Ni^{+2}$ (50) |

TABLE II-continued

| Sequesterant, product of | Metal (p.p.m.) sequestered per 60 p.p.m. sequesterant | |
| --- | --- | --- |
| Example 3 | $Fe^{+3}$ | (60) |
| | $Al^{+3}$ | (100) |
| | $Cu^{+2}$ | (90) |
| | $Ni^{+3}$ | (50) |

Other heavy metals sequestered by the sequestering agents of this invention such as cobalt, manganese, chromium and the like.

The amount employed to chelate is controlled by stoichiometry in contrast to scale inhibition where the amount employed is threshold or less than stoichiometric.

USE AS A MICROBIOCIDE (I) In water treatment

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

(II) Water flooding in secondary recovery of oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20-30 percent of the oil in a producing formation that is usually recovered in the primary process. In flooding operation, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Free plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

(III) Hydrocarbon treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

MICROBIOCIDAL TESTING

The screening procedure was as follows: a one percent by weight solution of the test compound in water was prepared. The solution was aseptically added to a sterile broth that would support the growth of the test organism, *Desulfovibro desulfuricans,* to provide the concentrations indicated by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 24 hours. The absence or presence of growth of the microorganisms was determined by visual inspection by an experienced observer.

Following is a summary of the results of the testing of examples of this invention.

| Compound Example Number | Concentration in p.p.m. | Results |
|---|---|---|
| 2 (Sodium salt) | 75 | *Gave control |
| 10 (Sodium salt) | 25 | " |
| 11 (Sodium salt) | 25 | " |

*By control is meant that the test compound was biostatic or biocidal - i.e., no growth of the test organism occurred under the test conditions.

USES IN ACID SYSTEMS

The compounds of this invention can also be employed as corrosion inhibitors for acid systems, for example as illustrated by the pickling of ferrous metals, the treatment of calcareous earth formations, etc., as described in the following sections.

USES

This invention also relates to the inhibition of corrosion, particularly the corrosion of metals in contact with the acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results will be experienced. There has been a continuing search for corrosion inhibitors which can be used effectively in small concentrations, and which are economical to produce. The need is also for corrosion inhibitors which are effective at high temperatures, e.g., 200° F. and above, such as are found in operations involving acidic solutions, particularly oil-well acidizing where higher and higher temperatures are found as the well extends further into the earth.

While the compounds of this invention are of themselves particularly good acid corrosion inhibitors, optionally they may be blended with acetylenic alcohols, dispersing and solubilizing agents such as ethoxylated phenols, alcohols, and fatty acids. They may also be blended with such known acid inhibitors as the quinoline or alkyl pyridine quaternary compounds or synergists such as terpene alcohols, formamide, formic acid, alkyl amine, alkylene polyamines, heterocyclic amines, and the like.

Quaternary ammonium compounds may be illustrated by C-alkyl pyridine-N-methyl chloride quaternary, C-alkyl pyridine-N-benzyl chloride quaternary, quinoline-N-benzyl chloride quaternary, isoquinoline-N-benzyl chloride quaternary, thioalkyl pyridine quaternaries, thioquinoline quaternaries, benzoquinoline quaternaries, thiobenzoquinoline quaternaries, imidasole quaternaries, pyrimidine quaternaries, carbazole quaternaries, the corresponding ammonium compounds, pyridines and quinolines may also be used alone or in combination with the quaternary compounds. Thus a pyridine plus quinoline quaternary, a quinoline plus quinoline quaternary, or quinoline or amine alone or in combination may be used.

The formic acid compound may be selected from the esters and amides of formic acid. The formic acid compound may be from the group consisting of formate esters of the structure:

HCOOR where R is a monoaryl group, an alkyl group having 1 to 6 carbon atoms, cyclo-alkyl residues having 5 to 6 carbon atoms, alkenyl and alknyl groups having 2 to 6 carbon atoms which may contain functional groupings selected from —C—OH, —OH, =C=O, —COOH, —SH, and NH$_2$. Examples of the formic acid compound are: methyl formate, ethyl-formate, benzyl formate, other alkyl and aryl formates, and the like. Other examples include formamide, dimethyl formamide, formanilide, and the like. Mixtures of the esters and mixtures of the amides may be used.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

CORROSION TEST PROCEDURE

In these tests the acid solutions were mixed by diluting concentrated hydrochloric acid with water to the desired concentrations.

Corrosion coupons of 1020 steel (AISI) were pickled in an uninhibited 10% HCl solution for 10 minutes, neutralized in a 10% solution of $NaHCO_3$, dipped in acetone to remove water and allowed to dry. They were then weighed to the nearest milligram and stored in a desicator.

In most of the tests, a 25 cc/in$^2$ acid volume to coupon surface area ratio was used. After the desired amount of acid was poured into glass bottles, the inhibitor was added. The inhibited acid solution was then placed in a water bath which had been set at a predetermined temperature and allowed to preheat for 20 minutes. After which time, the coupons were placed in the preheated inhibited acid solutions. The coupons were left in the acid solutions for the specified test time, then removed, neutralized, recleaned, rinsed, dipped in acetone, allowed to dry, then reweighed.

The loss in weight in grams was multiplied times a calculated factor to convert the loss in weight to lbs./ft$^2$/24 hrs. The factor was calculated as follows:

$$\frac{\frac{144 \text{ in}^2}{\text{ft}^2}}{\frac{454 \text{ g}}{\text{lb}} \times \text{Surface Area of Coupon (in}^2) \times \frac{1 \text{ day}}{24 \text{ hrs.}}} = \text{Factor}$$

| CORROSION INHIBITION IN 15% HCl | | | | |
|---|---|---|---|---|
| Inhibitor | p.p.m. | Test Temp. | Test Time | Corrosion Rate (lbs/ft$^2$/day) |
| 2 | 2000 | 150° F. | 4 hrs. | 0.079 |
| 10 | 2000 | 150° F. | 4 hrs. | 0.050 |
| 12 | 2000 | 150° F. | 4 hrs. | 0.048 |
| Blank | | 150° F. | 4 hrs. | 0.220 |

I claim:

1. A process of controlling the growth of microorganisms in aqueous or hydrocarbon systems which comprises treating said system with an effective amount of a compound having the formula

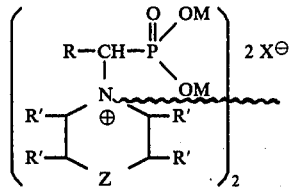

where R is alkyl, alkenyl, cycloalkyl, aryl, alkaryl, aralkyl or hydroxyphenyl, R' is hydrogen or alkyl, Z is S, SO or $SO_2$, M is hydrogen or a salt moiety, ⁓⁓⁓ is a bridging group selected from alkylene, aralkylene, alkaralkylene, alkylene- or polyalkylene ether, alkenylene or alkinylene and X is a halide.

2. The process of claim 1 where R' is hydrogen and Z is $SO_2$.

3. The process of claim 2 where R is alkyl, alkenyl, cycloalkyl, aryl, alkaryl aralkyl or hydroxyphenyl and is alkylene, aralkylene, alkaralkylene, alkylene- or polyalkylene ether, alkenylene or alkinylene.

4. The process of claim 3 where R is methyl, ethyl, propyl, hexyl, undecyl, heptadecyl, phenyl, hydroxyphenyl, tolyl, benzyl or cyclohexyl and ⁓⁓⁓ is $-(CH_2)_2-$, $-(CH_2)_4-$, $-(CH_2)_6-$, $-CH_2-CH=CH-CH_2-$ or

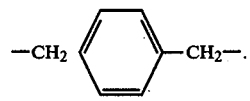

5. The process of claim 1 where the system treated is an aqueous system.

6. The process of claim 1 where the microorganism controlled is *Desulfovibrio desulfuricans*.

* * * * *

UNITED STATES PATENT AND TRADEMARK OFFICE
CERTIFICATE OF CORRECTION

PATENT NO. : 4,342,584
DATED : August 3, 1982
INVENTOR(S) : Patrick M. Quinlan

It is certified that error appears in the above—identified patent and that said Letters Patent is hereby corrected as shown below:

Claim 3, line 3:

The blur appearing at the beginning of line 3 should be a wavy line " ᴜᴄᴜᴄ " as it appears in claim 1, 2 and 4.

Signed and Sealed this

Twelfth Day of October 1982

[SEAL]

Attest:

Attesting Officer

GERALD J. MOSSINGHOFF
Commissioner of Patents and Trademarks